United States Patent [19]

Suzuki et al.

[11] Patent Number: 4,675,179

[45] Date of Patent: Jun. 23, 1987

[54] COSMETIC EMULSION AND METHOD FOR MAKING THE SAME

[75] Inventors: Toshiyuki Suzuki, Ichikawa; Akira Tsukada, Kodaira; Masanobu Kai, Funabashi, all of Japan

[73] Assignee: Kao Corporation, Tokyo, Japan

[21] Appl. No.: 701,518

[22] Filed: Feb. 14, 1985

[30] Foreign Application Priority Data

Mar. 16, 1984 [JP] Japan ................... 59-50547

[51] Int. Cl.$^4$ ................ A61K 7/36; A61K 7/38
[52] U.S. Cl. ........................ 424/67; 424/68; 514/941
[58] Field of Search .......... 514/63, 941; 424/70, 424/66, 68, 67, 63

[56] References Cited

U.S. PATENT DOCUMENTS

| | | | |
|---|---|---|---|
| 3,641,239 | 2/1972 | Mohrlok | 514/63 |
| 3,655,865 | 4/1972 | Murphy | 514/63 |
| 4,254,104 | 3/1981 | Suzuki | 514/63 |
| 4,264,586 | 4/1981 | Callingham et al. | 424/68 |
| 4,268,499 | 5/1981 | Keil | 424/68 |
| 4,311,695 | 1/1982 | Starch | 514/63 |
| 4,423,032 | 12/1983 | Abe et al. | 514/63 |
| 4,423,041 | 12/1983 | Chem et al. | 514/63 |
| 4,554,369 | 11/1985 | Hill et al. | 424/59 |

FOREIGN PATENT DOCUMENTS

| | | | |
|---|---|---|---|
| 0022712 | 3/1981 | Japan | 424/70 |
| 0086113 | 7/1981 | Japan | 424/70 |
| 803289 | 10/1958 | United Kingdom | 514/63 |

*Primary Examiner*—Dale R. Ore
*Attorney, Agent, or Firm*—Oblon, Fisher, Spivak, McClelland & Maier

[57] ABSTRACT

A cosmetic emulsion of low viscosity which comprises (a) 0.2 to 5 wt % of an emusifier, (b) 0.5 to 10 wt % of an oil and (3) 85 to 99.3 wt % of a water phase. The emusifier (a) consists essentially of a dimethylpolysiloxane-polyalkylene copolymer, a surface active agent having an HLB value not smaller than 10, and a linear, saturated higher alcohol having from 12 to 22 carbon atoms. The relative ratios of the dimethylpolysiloxane-polyoxyalkylene copolymer, the surface active agent and the higher alcohol lie within the polygon bounded by the points of a ternary composition diagram of the annexed figure.

When the emulsion is applied to the skin, it gives refreshing feeling to the skin without any stickiness. It also gives appropriate moisture retentivity to the skin.

6 Claims, 1 Drawing Figure

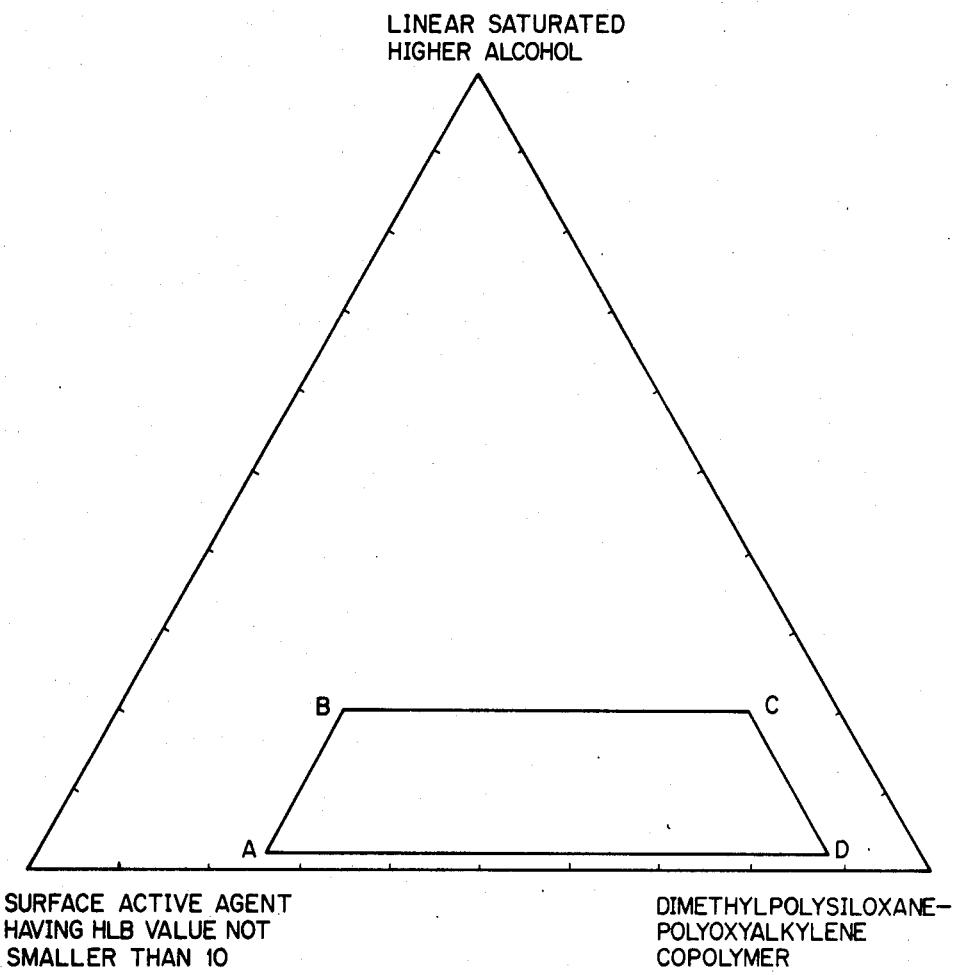
FIGURE

COSMETIC EMULSION AND METHOD FOR MAKING THE SAME

BACKGROUND OF THE INVENTION (i) Field of The Invention

This invention relates to stable, low viscosity cosmetic emulsions which have the skin refreshed upon application thereof without becoming sticky after the application and which have appropriate moisture retentivity. The invention also relates to a method for making such emulsions.

(ii) Description of the Prior Art

In general, cosmetic emulsions consist of water, oils and emulsifiers and, when applied to the skin, they form an oil film on the surface of the skin. By the coverage with the oil film, a percutaneous water loss is so suppressed that moisture in the horny layer is appropriately retained. The moisture-retentive effect depends on the type and amount of the oil, and thus the type and amount of the oil are suitably controlled according to the purposes.

In order to attain less stickiness and refreshness to the touch by the use of emulsions, it is necessary to reduce the amount of oils and use oils which are less sticky.

The polysiloxane of the general formula (II), (III) or (IV) indicated hereinafter (hereinafter referred to silicone oil) is able to form a uniform thin film on the skin and is suitable as an oil imparting the stickness-free smoothness to the touch. However, the silicone oil is rather poor in compatibility with ordinary surface active agents and other oils and has very poor ability of being emulsified, which makes it very difficult to obtain uniform, fine emulsions.

Better stability against coalescence and creaming is otained when emulsified particles are more uniform and finer. This tendency becomes more pronounced particularly when the viscosity of the system is low. The state of emulsification takes part in the appearance or whiteness of an emulsion. In this sense, optimal results are obtained when the particle size is in the range of from 0.2 to 2 $\mu$m. At a smaller particle size, there is obtained a transparent, pale microemulsion. Over the above range, a semitransparent, greyish emulsion is obtained.

In order to further impart refreshness at the time of application, the cosmetic system is preferred to contain ethyl alcohol. In general, addition of ethyl alcohol results in a considerable lowering of emulsion stability of the system.

The emulsion system having such properties as described above should satisfy the following requirements: ethyl alcohol is contained in an aqueous phase; an oil being emulsified is mainly composed of silicone oil and is contained in small amounts; and the system is low in viscosity and has emulsified particles which are fine and uniform in size. However, known emulsification techniques cannot satisfy all the above requirements at the same time.

SUMMARY OF THE INVENTION

Under these circumstances, the present inventors have made intensive studies to obtain cosmetic emulsions for which the objects of the invention can be achieved. As a result, it has been found that when a mixture of a specific type of dimethylpolysiloxane-polyoxyalkylene copolymer, a surface active agent having an HLB value not smaller than 10, and a linear, saturated higher alcohol having from 12 to 22 carbon atoms is used as an emulsifier, to which an aqueous phase comprising ethyl alcohol in a predetermined concentration is added under agitation in a predetermined range of temperature thereby forming one phase region of a gel or a highly viscous liquid, there can be obtained an emulsion with a low viscosity which is fine, uniform and stable and which contains the silicone oil as the main component. In addition, the emulsion composition satisfies the requirements for the cosmetic emulsion. The present invention is based on the above finding.

According to one feature of the invention, there is provided a cosmetic emulsion which comprises:

(a) 0.2 to 5 wt% of an emulsifier consisting essentially of (1) a dimethylpolysiloxane-polyoxyalkylene copolymer represented by the general formula (I)

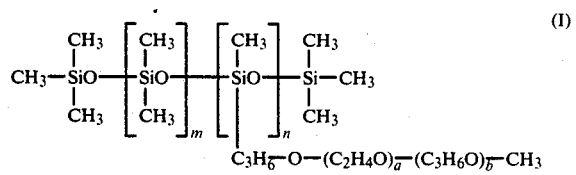

in which a represents an integer of from 10 to 25, b is an integer of from 25 to 35, m is an integer of from 60 to 80, and n is an integer of from 3 to 8, (2) a surface active agent having an HLB value not smaller than 10, and (3) a linear, saturated higher alcohol having from 12 to 22 carbon atoms;

(b) 0.5 to 10 wt% of an oil comprising 90% or more of at least one polysiloxane represented by the general formula (II), (III) or (IV)

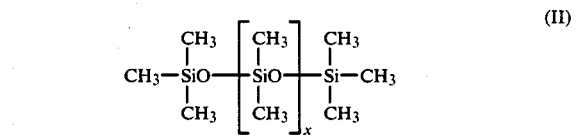

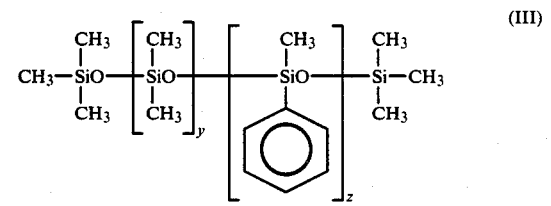

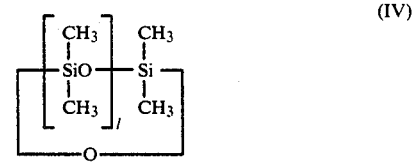

in which x represents an integer of from 4 to 100, z is an integer not smaller than 1, y+z is a value from 1 to 100, and l is an integer of from 2 to 5; and (c) 85 to 99.3 wt% of a water phase comprising 60 to 100 wt%, based on the total water phase, of an ethyl alcohol aqueous solution in which an ethyl alcohol to water ratio by weight is 50:50 to 2:98.

Another feature of the invention resides in provision of a method of making the cosmetic emulsion.

BRIEF DESCRIPTION OF THE DRAWING

The sole FIGURE is a ternary composition diagram showing relative ratios of dimethylpolysiloxane-polyoxyalkylene copolymer, a surface active agent having an HLB value not smaller than 10, and a linear, saturated higher alcohol having 12 to 22 carbon atoms, which constitute an emulsifier of a cosmetic emulsion of the invention.

DETAILED DESCRIPTION OF THE INVENTION AND PREFERRED EMBODIMENTS

The dimethylpolysiloxane-polyoxyalkylene copolymer of (1), which is one component of the emulsifier (a) of the cosmetic emulsion according to the invention, should preferably have a clouding point, as an aqueous solution thereof, of 25° to 40° C. If the clouding point of the aqueous solution exceeds 50° C., one phase emulsion cannot be formed during the emulsification and the emulsified particles of the emulsion become coarse. On the other hand, when the clouding point is lower than 20° C., it does by no means serve as a surface active agent and thus no emulsification proceeds. The surface active agent (2) may be those agents having an HLB value not smaller than 10, which may be used singly or in combination. In particular, surface active agents having an HLB value of from 11 to 16 are preferred. Specific examples of the surface active agents include polyoxyethylene alkyl ethers, polyoxyethylene and fatty acid esters, fatty acid esters of polyoxyethylene and sorbitan, fatty acid esters of polyoxyethylene and glycerine, polyoxyethylene hardened castor oils, polyglycerine and fatty acid esters, sucrose and fatty acid esters, and the like.

The linear, saturated higher alcohols (3) should have from 12 to 22 carbon atoms, preferably 14 to 18 carbon atoms. When the number of carbon atoms are below 10, the action of stabilizing a material being emulsified lowers to a substantial extent with offensive odor. When the number of carbon atoms exceeds 22, there is the tendency toward crystallization as time passes.

The emulsifier which is component (a) should preferably have relative ratios of (1), (2) and (3) within a polygon (including each side thereof) bounded by the points A(25:73:2), B(25:55:20), C(70:10:20) and D(88:10:2) of the ternary composition diagram of the sole FIGURE. The emulsifier is used in an amount of 0.2 to 5 wt% (hereinafter referred to simply as %) of the cosmetic emulsion and preferably in an amount of 0.4 to 3%. Outside the range, the emulsification does not proceeds satisfactorily.

The oil component (b) should contain 90% or more of at least one silicone oil represented by the general formula (II), (III) or (IV). Aside from these silicone oils, there may be used hydrocarbons such as liquid paraffin, paraffin wax, ceresin, squalane and the like, natural animal and plant oils such as olive oil, jojoba oil, mink oil and the like, and synthetic ester oils such as octyldodecyl myristate. These oils are used in an amount of 0.5 to 10%, preferably 1 to 5%, of the cosmetic emulsion. Over 10%, oiliness is unfavorably strengthened.

The aqueous phase (c) should have a ratio by weight of ethyl alcohol and water in the range of 50/50 to 2/98. The ratio is preferably in the range of 30/70 to 5/95. When the ethyl alcohol/water ratio exceeds 50/50, the emulsification becomes unstable and the resulting emulsion is more stimulative against the skin. If, on the contrary, the ratio of ethyl alcohol/water is smaller than 2/98, refreshness does not appear. The aqueous phase may further comprise humectants such as glycerin, sorbitol, maltitol propylene glycol, dipropylene glycol, 1, 3-butylene glycol, sodium pyrrolidonecarboxylate, polyoxyethylene methylglucoside, polyoxypropylene methylglucoside, glucose and the like amino acids such as glycine, serine, proline and the like, and medical agents such as antiinflammatory agents, bactericides, vitamins and the like. The aqueous phase is used in an amount of 85 to 99.3%, preferably 92 to 98.6%, of the cosmetic emulsion.

The cosmetic emulsion of the invention is preferred to be low in viscosity and has generally a viscosity of below 100° centipoises at 25° C., preferably below 20 centipoises. Over 100 centipoises, the resulting emulsion is felt sticky upon application thereof.

The cosmetic emulsion of the invention is prepared by the procedure which comprises adding an ethyl alcohol aqueous solution, which has an ethyl alcohol/water ratio by weight of 20/80 to 70/30, to a mixture of (a) 0.2 to 5 parts by weight of an emulsifier and (b) 0.5 to 10 parts by weight of an oil under agitation at a temperature of from 20° to 45° C. to produce an o/w emulsion, and, if necessary, further adding water or an ethyl alcohol aqueous solution to give an intended composition.

In the practice of the invention, when the ethyl alcohol aqueous solution having an ethyl alcohol/water ratio by weight of 20/80 to 70/30, preferably 30/70 to 60/40, is added in an amount of 0.5 to 5 times by weight the mixture of (a) and (b), a gellike or highly viscous liquid one phase product is produced. Further addition of ethyl alcohol results in an o/w emulsion. If necessary, water or an ethyl alcohol aqueous solution is so added that the ratio by weight of ethyl alcohol/water is in the range of 50/50 to 2/98. The finally added water or ethyl alcohol aqueous solution should preferably be controlled at a temperature of from 5 to 45° C.

One of features of the invention resides in that one phase region is formed by emulsification using a high content of ethanol, through which region uniform and fine emulsified particles are obtained. The fact that fine emulsified particles are obtained through the one phase region during the course of the emulsification is known per se with regard to ordinary oil/emulsifier/water systems and oil/emulsifier/water/dihydric alcohol systems ("Journal of Chemical Society of Japan, 10, 1399 (1983), by Sagitani). The method for making cosmetic emulsions according to the invention is different from these known methods in that one phase region is formed under conditions of a high ethyl alcohol concentration in the system comprising an oil chiefly made of silicone oil, thereby obtaining a stable, low viscosity emulsion composition comprising fine, uniform emulsified particles. Moreover, it is also known from, for example, Japanese Laid-open Patent Application No. 58-131910 that polydiorganosiloxane-polyoxyalkylene copolymers are effective for emulsifying silicone oils. The present invention is also different from this prior art in that the emulsifier useful in the present invention consists of dimethylpolysiloxane-polyoxyalkylene copolymer, a surface active agent having an HLB value not smaller than 10, and a linear, saturated higher alcohol having from 12 to 22 carbon atoms in specific ratios, that an aqueous solution of the dimethylpolysiloxane-polyoxyalkylene copolymer has such a low clouding point of from 20° to 45° C. that it does not serve as an emulsifier under ordinary emulsifying conditions, but shows good performance as the emulsifier by defining the content of ethyl alcohol and the emulsification temperature in certain ranges, respectively.

The present invention is described by way of examples.

EXAMPLE 1

Cosmetic emulsions having the formulations indicated in Table 1 were prepared to check the emulsion stability. The results are shown in Table 2.

TABLE 1

| | Composition (%) | | | | | | |
|---|---|---|---|---|---|---|---|
| | Products of Invention | | | Comparative Products | | | |
| Ingredients | A | B | C | D | E | F | G |
| Oil Phase: | | | | | | | |
| Dimethylpolysiloxane-polyoxyalkylene copolymer (clouding point: 30° C.) | 0.5 | 0.5 | 0.93 | 0.5 | — | 0.5 | 0.81 |
| Dimethylpolysiloxane-polyoxyalkylene copolymer (clouding point: 80° C.) | — | — | — | — | 0.5 | — | — |
| POE(20) Sorbitan monooleate (HLB: 15) | 0.5 | 0.4 | 0.12 | 0.2 | 0.5 | — | 0.28 |
| Sorbitan monooleate (HLB: 4.3) | — | — | — | — | — | 0.5 | — |
| Cetanol | 0.1 | 0.08 | 0.05 | 0.4 | 0.1 | 0.1 | 0.01 |
| Dimethylpolysiloxane | 1.5 | 2 | 1.5 | 1.5 | 1.5 | 1.5 | 1.5 |
| Methylphenylpolysiloxane | 1.5 | — | 1.5 | 1.5 | 1.5 | 1.5 | 1.5 |
| Perfume | small amount | small amount | small amount | small amount | small amount | small amount | small amount |
| Alcohol Phase: | | | | | | | |
| Ethyl alcohol | 10 | 20 | 10 | 10 | 10 | 10 | 10 |
| Water | 10 | 25 | 10 | 10 | 10 | 10 | 10 |
| Glycerine | 3 | 2 | 3 | 3 | 3 | 3 | 3 |
| Aqueous Phase: | | | | | | | |
| Water | balance | balance | balance | balance | balance | balance | balance |

Preparation: The oil phase was heated to 60° C. and all the ingredients were uniformly dissolved, followed by cooling down to 36° C. and keeping at a constant level. To the oil phase was added under agitation the alcohol phase which was controlled at 36° C. Thereafter, the aqueous phase of 25° C. was added to the mixture to give an intended composition.

TABLE 2

| | State of Emulsion | Stability (preserved for 1 month) | |
|---|---|---|---|
| Products of Invention: | | | |
| A | good | 40° C. | no change |
| | | 5° C. | no change |
| B | good | 40° C. | no change |
| | | 5° C. | no change |
| C | good | 40° C. | no change |
| | | 5° C. | no change |
| Comparative Products: | | | |
| D | rather poor | 40° C. | separation |
| | | 5° C. | separation as crystals |
| E | separated immediately after preparation | | |
| F | separated immediately after preparation | | |
| G | rather poor | 40° C. | separation |
| | | 5° C. | separation |

As will be clear from Table 2, the cosmetic emulsions of the invention showed good stability.

EXAMPLE 2

Emulsion compositions of the formulations indicated in Table 3 were prepared to check the emulsion stability and viscosity. The results are shown in Table 4. The preparation of each emulsion was made in the same manner as in Example 1.

TABLE 3

| | Composition (%) | | | | | | | |
|---|---|---|---|---|---|---|---|---|
| | Products of Invention | | Comparative Products | | | | | |
| Ingredients | H | I | J | K | L | M | N | O |
| Oil Phase: | | | | | | | | |
| Dimethylpolysiloxane-polyoxyalkylene copolymer (clouding point: 30° C.) | 0.5 | 0.3 | 0.3 | 0.3 | 0.3 | 0.3 | 0.3 | 0.3 |
| POE(20) hexadecyl ether (HLB: 16) | 0.4 | 0.5 | 0.5 | 0.5 | 0.5 | 0.5 | 0.5 | 0.5 |
| Cetostearyl alcohol | 0.1 | 0.2 | 0.2 | 0.2 | 0.2 | 0.2 | 0.2 | 0.2 |
| Methylphenylpolysiloxane | 1.0 | 1.0 | 1.0 | 10.0 | 1.0 | 1.0 | 1.0 | 1.0 |
| Cyclic dimethylpolysiloxane | 2.0 | 1.0 | — | 6.0 | 1.0 | 1.0 | 1.0 | 1.0 |
| Octyldodecyl myristate | 0.2 | — | 1.0 | — | — | — | — | — |
| Perfume | small amount | small amount | small amount | small amount | small amount | small amount | small amount | small amount |
| Alcohol Phase: | | | | | | | | |
| Ethyl alcohol | 8 | 15 | 15 | 15 | 50 | 15 | — | 1.5 |
| Water | 12 | 15 | 15 | 15 | 30 | 3 | 15 | 5 |

TABLE 3-continued

| | Composition (%) | | | | | | | |
|---|---|---|---|---|---|---|---|---|
| | Products of Invention | | Comparative Products | | | | | |
| Ingredients | H | I | J | K | L | M | N | O |
| Dipropylene glycol | 4 | 3 | 3 | 3 | 3 | 3 | 3 | 3 |
| Aqueous Phase: | | | | | | | | |
| Water | balance | balance | balance | balance | balance | balance | balance | balance |

TABLE 4

| | Emulsion State (immediately after preparation) | Stability (preserved for 1 month) | | Viscosity (25° C.) (cps.) |
|---|---|---|---|---|
| Products of Invention: | | | | |
| H | good | 40° C. | no change | 6 |
| | | 5° C. | no change | |
| I | good | 40° C. | no change | 4 |
| | | 5° C. | no change | |
| Comparative Products: | | | | |
| J | good | 40° C. | separation | 4 |
| | | 5° C. | separation | |
| K | rather poor | 40° C. | separation | 600 |
| | | 5° C. | no change | |
| L | good | 40° C. | separation | 3 |
| | | 5° C. | separation | |
| M | separated immediately after preparation | — | | — |
| N | separated immediately after preparation | — | | — |
| O | rather poor | 40° C. | separation | 6 |
| | | 5° C. | separation | |

As will be clear from Table 4, the cosmetic emulsions of the invention showed good stability though very low in viscosity.

EXAMPLE 3

Five samples, in total, including the cosmetic emulsion A obtained in Example 1 and the cosmetic emulsion I of Example 2, both of which were the products of the invention, and the comparative emulsions J, K and O of Example 2 were organoleptically evaluated by 10 expert panelers with regard to the feelings to the touch. The results are shown in Table 5 below.

TABLE 5

| | Refreshness | Stickiness | Oiliness | Affinity | Appearance |
|---|---|---|---|---|---|
| Products of Invention | | | | | |
| A | 1.6 | −0.8 | −1.2 | +1.5 | +1.8 |
| I | 2.0 | −1.6 | −1.9 | +1.4 | +1.6 |
| Comparative Products: | | | | | |
| J | 2.0 | +1.1 | −0.5 | −0.2 | +1.6 |
| K | 1.8 | +0.8 | +1.7 | −1.4 | −1.0 |
| O | −0.8 | −1.4 | −0.8 | +0.4 | −1.6 |
| Evaluation Standard: | | | | | |
| | Refreshness | Stickiness | Oiliness | Affinity for Skin | Appearance |
| +2 | Very good | Very great | Very great | Very good | Very good |
| +1 | Rather good | Rather great | Rather great | Rather good | Rather good |
| 0 | Moderate | Moderate | Moderate | Moderate | Moderate |
| −1 | Bad | Small | Small | Rather poor | Rather poor |
| −2 | Very bad | Very small | Very small | Very poor | Very poor |

(The values are average values of ten panelers.)

As will be seen from Table 5, the products of the invention are better in refreshness, less in stickiness and oiliness, and better in affinity for skin and appearance than the comparative products.

EXAMPLE 4

Emulsion compositions P, Q of the invention having formulations indicated in Table 6, a comparative product R free of any oils, and commercially sold lotion S were each applied onto the flexor side of the forearm of men, followed by measurement of a skin conductance. The skin conductance corresponds to a constant of water in the epidermic corneum, meaning a greater amount of water at a higher conductance value. The measurement was effected using a high frequency impedance meter (Capacitance-conductance Meter Model 354, by IBS Co., Ltd.). The results are shown in Table 7 below.

TABLE 6

| | Composition (%) | | |
|---|---|---|---|
| | Products of Invention | | Comparative Product |
| Ingredients | P | Q | R |
| Oil Phase: | | | |
| Dimethylpolysiloxane-polyoxyalkylene copolymer (clouding point: 28° C.) | 0.4 | 0.4 | — |
| POE(60) hardened caster oil (HLB: 14.5) | 0.9 | 0.9 | 0.9 |
| Stearyl alcohol | 0.1 | 0.1 | — |
| Dimethylpolysiloxane | 2.5 | 2.5 | — |
| Methylphenylpolysiloxane | 1 | 1 | — |
| Perfume | small amount | small amount | small amount |
| Alcohol phase: | | | |
| Ethyl alcohol | 12 | 12 | 12 |
| Water | 16 | 16 | 16 |
| Glycerine | 4 | — | 4 |
| Aqueous phase: | | | |
| Water | balance | balance | balance |

(The comparative product R was a transparent liquid, not an emulsion.)

Preparation: Prepared in the same manner as in Example 1.

TABLE 7

| | Time after Application of Tested Sample (Minutes) | | | | |
|---|---|---|---|---|---|
| Tested Sample | 10 | 30 | 60 | 90 | 120 |
| Products of Invention: | | | | | |
| P | 360 | 320 | 298 | 316 | 300 |
| Q | 336 | 293 | 288 | 280 | 288 |
| Comparative Products: | | | | | |
| R | 170 | 100 | 98 | 95 | 92 |
| S | 133 | 91 | 88 | 87 | 83 |
| (Commercial available lotion) | | | | | |
| Control (nothing applied on | 82 | 82 | 80 | 83 | 80 |

TABLE 7-continued

| Tested Sample | Time after Application of Tested Sample (Minutes) | | | | |
|---|---|---|---|---|---|
| | 10 | 30 | 60 | 90 | 120 |
| the skin) | | | | | |

Unit: $\mu v/cm$

As will be seen from Table 7, the cosmetic emulsions of the invention show a higher skin moisture-retentive effect than the comparative product R and the commercial lotion.

EXAMPLE 5

The cosmetic emulsion A obtained in Example 1 which is a product of the invention was used but prepare in different manners to determine the state and stability of the resulting emulsions. The preparatory procedures are summarized in Table 8 with the results shown in Table 9 below.

TABLE 8

| Preparation Procedure | |
|---|---|
| Comparative Products: | |
| T | Prepared in the same manner as in Example 1 but, at the time of emulsification, the oil and alcohol phases were set at 50° C. when emulsified. |
| U | Prepared in the same manner as in Example 1 but, at the time of emulsification, the alcohol and aqueous phases were first mixed together and then used for emulsification. |
| V | Prepared in the same manner as in Example 1 but, at the time of emulsification, the oil phase was added to the alcohol phase, followed by adding the water phase. |
| W | Prepared in the same manner as in Example 1 but, at the time of emulsification, the water phase was first added, followed by adding the alcohol phase. |

TABLE 9

| Emulsion State (immediately after preparation) | Average Size of Emulsified Particles ($\mu m$) | Stability (preserved at room temperature for 2 months) |
|---|---|---|
| Product of Invention: | | |
| A  good | 0.5 | no change |
| Comparative Products: | | |
| T  rather poor | 8.6 | separation |
| U  rather poor | 12 | separation |
| V  rather poor | 17 | separation |
| W  separated immediately after preparation | — | — |

For the measurement of the particle size, there were used Coulter counter Model TA-II and Coulter submicronanalyzer Model N4.

EXAMPLE 6 (Astringent Milk)

| Ingredients | Formulation (%) |
|---|---|
| Oil Phase: | |
| Dimethylpolysiloxane-polyoxyalkylene copolymer (clouding point: 30° C.) | 0.5 |
| POE(20) hexadecyl ether | 0.5 |
| Cetanol | 0.1 |
| Dimethylpolysiloxane | 2.0 |
| Perfume | small amount |
| Alcohol Phase: | |
| Ethyl alcohol | 20 |
| Water | 20 |
| 1,3-Butylene glycol | 3 |
| Citric acid | 0.1 |
| Zinc paraphenolsulfonate | 0.1 |
| Aqueous Phase: | |
| Water | balance |

Preparation: same as in the procedure of Example 1.

EXAMPLE 7 (Moisture Milk)

| Ingredients | Formulation (%) |
|---|---|
| Oil Phase: | |
| Dimethylpolysiloxane-polyoxyalkylene copolymer (clouding point: 32° C.) | 0.8 |
| POE(60) hardened castor oil | 1.2 |
| Setostearyl alcohol | 0.2 |
| Methylphenylpolysiloxane | 6 |
| Vaseline | 0.5 |
| Perfume | small amount |
| Alcohol Phase: | |
| Ethyl alcohol | 6.0 |
| Glycerine | 4.0 |
| Maltitol | 2.0 |
| Water | 10 |
| Aqueous Phase: | |
| Water | balance |

Preparation: same in the procedure of Example 1.

EXAMPLE 8 (Anhidrotic Lotion)

| Ingredients | Formulation (%) |
|---|---|
| Oil Phase: | |
| Dimethylpolysiloxane-polyoxyalkylene copolymer (clouding point: 28° C.) | 0.5 |
| POE(20) hexadecyl ether | 0.2 |
| Stearyl alcohol | 0.1 |
| Volatile cyclic silicone | 1.5 |
| Dimethylpolysiloxane | 0.5 |
| Perfume | small amount |
| Alcohol Phase: | |
| Ethyl alcohol | 40 |
| Water | 50 |
| Aluminium hydroxychloride | 5 |
| Aqueous Phase: | |
| Water | balance |

Preparation: same as in the procedure of Example 1.

What is claimed for patent is:

1. A cosmetic emulsion comprising:
(a) 0.2 5 wt% of an emulsifier consisting essentially of
   (1) a dimethylpolysiloxane-polyoxyalkylene copolymer represented by the general formula (I)

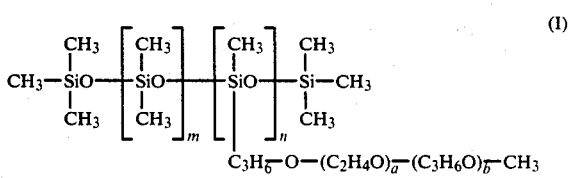

in which a represents an integer of from 10 to 25, b is an integer of from 25 to 35, m is an integer of from 60 to 80, and n is an integer of from 3 to 8, wherein an aqueous solution of said copolymer has a clouding point of from 20° to 45° C., (2) a surface active agent having an HLB value not smaller than 10, and (3) a linear, saturated higher alcohol having more 12 to 22 carbon atoms;

(b) 0.5 to 10 wt% of an oil comprising 90% or more of at least one polysiloxane represented by the general formula (II), (III) or (IV)

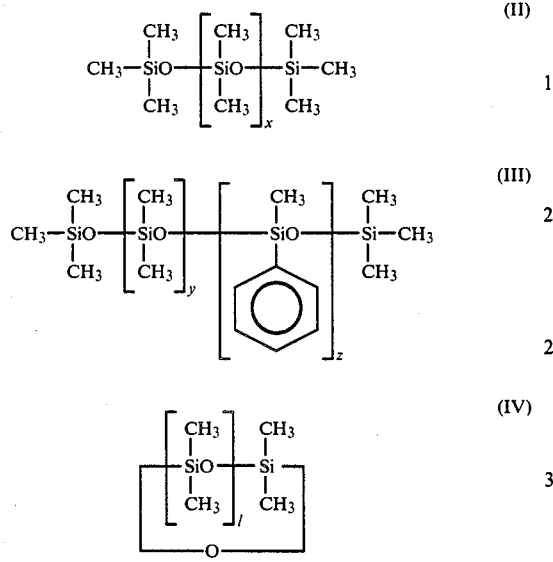

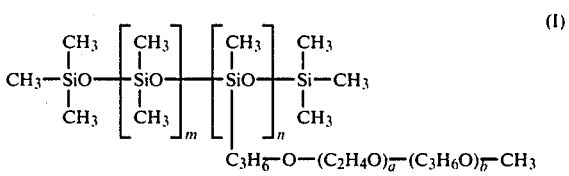

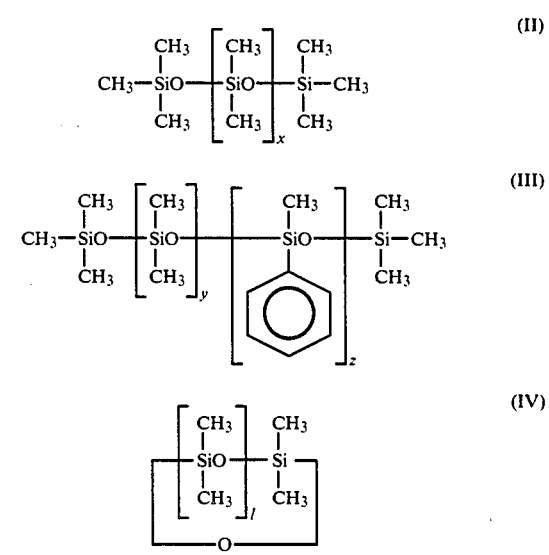

in which x represents an integer of from 4 to 100, z is an integer not smaller than 1, y+z is a value from 1 to 100, and l is an integer of from 2 to 5; and (c) 85 to 99.3 wt% of a water phase comprising 60 to 100 wt%, based on the total water phase, of an ethyl alcohol aqueous solution in which an ethyl alcohol to water ratio by weight is 50:50 to 2:98, wherein said cosmetic emulsion has a viscosity of below 100 centipoises at 25° C.

2. A cosmetic emulsion according to claim 1, wherein relative ratios of the dimethylpolysiloxane-polyoxyalkylene copolymer, the surface active agent having an HLB value not smaller than 10 and the linear saturated higher alcohol having from 12 to 22 carbon atoms lie within a polygon (including each side) bounded by the points of a ternary composition diagram of the annexed sole FIGURE.

3. A cosmetic emulsion according to any of claims 1 through 2, wherein said cosmetic emulsion has a viscosity of below 100 centipoises at 25° C.

4. A method for making a cosmetic emulsion which comprises, as essential components,
(a) 0.2 to 5 wt% of an emulsifier consisting essentially of (1) a dimethylpolysiloxane-polyoxyalkylene copolymer in which a represents an integer of from 10 to 25, b is an integer of from 25 to 35, m is an integer of from 60 to 80, and n is an integer of from 3 to 8, (2) a surface active agent having an HLB value not smaller than 10, and (3) a linear, saturated higher alcohol having from 12 to 22 carbon atoms;

(b) 0.5 to 10 wt% of an oil comprising 90% or more of at least one polysiloxane represented by the general formula (II), (III) or (IV)

in which x represents an integer of from 4 to 100, z is an integer not smaller than 1, y+z is a value from 1 to 100, and l is an integer of from 2 to 5; and (c) 85 to 99.3 wt% of a water phase comprising 60 to 100 wt%, based on the total water phase, of an ethyl alcohol aqueous solution in which an ethyl alcohol to water ratio by weight is 50:50 to 2:98, the method comprising the steps of adding the ethyl alcohol aqueous solution having an ethylalcohol/water ratio by weight in the range of 20/80 to 70/30, to a mixture of 0.2 to 5 parts by weight of the emulsifier (a) and 0.5 to 10 parts by weight of the oil (b) at a temperature of from 20° to 45° C. under agitation, thereby obtaining an o/w emulsion, and, optionally, further adding water or an ethyl alcohol aqueous solution to the o/w emulsion to give a cosmetic emulsion composition.

5. The cosmetic emulsion of claim 1, wherein the surface active agent has an HLB value of from 11 to 16.

6. A cosmetic emulsion according to claim 2, wherein said cosmetic emulsion is in the form of an astringent milk, moisture milk, or anhidrotic lotion.

* * * * *